(12) United States Patent
Nnanna et al.

(10) Patent No.: US 6,995,242 B2
(45) Date of Patent: Feb. 7, 2006

(54) PROCESS FOR PRODUCING INSOLUBLE AND SOLUBLE COLLAGEN PROTEIN PRODUCTS FROM POULTRY SKINS AND USE THEREOF

(75) Inventors: Ifendu Nnanna, Ames, IA (US); Allen Leinen, Ames, IA (US); David Hull, Ames, IA (US)

(73) Assignee: The Lauridsen Group, Inc., Ankeny, IA (US)

( * ) Notice: Subject to any disclaimer, the term of this patent is extended or adjusted under 35 U.S.C. 154(b) by 350 days.

(21) Appl. No.: 10/195,193

(22) Filed: Jul. 15, 2002

(65) Prior Publication Data

US 2004/0010122 A1    Jan. 15, 2004

(51) Int. Cl.
*A61K 38/17* (2006.01)
*C07K 14/00* (2006.01)

(52) U.S. Cl. ............... 530/356; 530/354; 530/355; 530/412; 530/418

(58) Field of Classification Search .......... 530/356, 530/354, 355, 412, 418
See application file for complete search history.

(56) References Cited

U.S. PATENT DOCUMENTS

| | | |
|---|---|---|
| 2,979,438 A | 4/1961 | Highberger |
| 3,034,852 A | 5/1962 | Nishihara |
| 3,398,677 A | 8/1968 | Theobald et al. |
| 4,176,199 A * | 11/1979 | Vollmer et al. ............ 426/59 |
| 4,295,894 A | 10/1981 | Cioca et al. |
| 4,894,441 A | 1/1990 | Menicagli |
| 4,980,403 A | 12/1990 | Bateman et al. |
| 5,071,665 A | 12/1991 | Buckley et al. |
| 5,162,506 A | 11/1992 | Hadden |
| 6,016,862 A | 1/2000 | Herreid |

* cited by examiner

*Primary Examiner*—Jon Weber
*Assistant Examiner*—Abdel A. Mohamed
(74) *Attorney, Agent, or Firm*—Schwegman, Lundberg, Woessner & Kluth, P.A.

(57) ABSTRACT

A method of extracting and fractionating collagen-rich proteinaceous materials and derivatives from poultry skin tissue and the development of the proteinaceous materials to collagen-based protein ingredients that can function as meat replacer, texturizer, binder/filler, stabilizer, or protective colloids in processed meat products. The insoluble and soluble collagen products, collagen-based protein ingredients, water-dispersible collagen-based protein ingredients are produced by heating, separating, and rapidly cooling the solid-phase below its melting temperature to exploit reformation of the helical forms which produces a high concentration of coils, a phenomenon that accounts for its ability to form cold-set thermal reversible gels and gel strength.

26 Claims, No Drawings

PROCESS FOR PRODUCING INSOLUBLE AND SOLUBLE COLLAGEN PROTEIN PRODUCTS FROM POULTRY SKINS AND USE THEREOF

BACKGROUND OF THE INVENTION

This invention relates to a process for producing insoluble collagen products, collagen-based protein ingredients, water-dispersible collagen-based protein ingredients, and reduced-fat collagen-rich protein ingredients from animal skins tissues, particularly, poultry skin tissues. The ideas of converting pig skin, cowhide, and animal bones to commercial products, leather, collagen, and gelatin are well-established art. Information relevant to attempts to address these problems can be found in U.S. Pat. Nos. 2,979,438; 4,176,199; 3,398,677; 4,295,894; and Ockerman, H. W. and Hansen, C. L., Animal By-Product Processing and Utilization (2000). In the embodiments of the present invention, an unconventional technique was used in a new application, that is, poultry skins. In the production of skinless turkey and chicken products, skins and skins containing adhering muscle flesh are by-products. The use of these by-products are very limited. In recent years, there has been a need to add value to million of tons of poultry skins produced annually, a valuable source of potential revenue for both the poultry meat producer and the ingredient manufacturer. With U.S. broiler meat and turkey meat production reaching billions of pounds, the tremendous tonnage of poultry skins as by-products that would otherwise be disposed of or undervalued as inedible rendered fractions, renders a need to convert such by-products to value-added collagen-based protein ingredients.

Collagen is the most abundant protein in mammals (See U.S. Pat. No. 5,043,426 to Goldstein). Chemically, collagen is the fibrous protein that contributes to the unique physiological functions of connected tissues in the skin, tendon, bones, and cartilage. The structural unit is tropocollagen composed of 3-polypeptide chains, designated $\alpha 1$, $\alpha 2$, and $\alpha 3$, that form a triple helical structure stabilized by hydrogen bonds. This structure accounts for its rod-like form and rigid properties. The amino acid sequence of collagen is remarkably regular; nearly every third residue is glycine (gly-x-y triplet) in a region spanning more than 1,000 residues. Collagen molecules contain approximately 33% glycine, 22% proline, 11% hydroxyproline, and 0.7% hydroxylysine. From a nutritional standpoint, collagen is devoid of tryptophan, low in methionine, cysteine and tyrosine. Collagen contains two uncommon amino acids, 4-hydroxyproline and 5-hydroxylysine. Additionally, collagen Type I, is the most abundant form of collagen, with widespread distribution within the body. While the skin is composed mostly of Type I collagen, it is not unlikely to find Types II and III.

Collagen denatures at temperatures above 4° Celsius to a mixture of random coils comprising single, double, and triple strands. Upon controlled cooling below the melting temperature, Tm, reformation of the helical forms occurs, a phenomenon that accounts for its ability to form cold-set thermal reversible gels. Also, collagen swells out, but does not solubilize in water per se. Rather, acid, base, heat, and certain protease enzymes are used to facilitate solubility. Common sources of collagen are animal hides, skins, and bones. These sources represent commercial raw materials for leather or gelatin production. The unique physiochemical characteristics of collagen enable their use in a variety of food and pharmaceutical products.

Each year, over 200,000 metric tons of animal-derived collagen and gelatin are used in foods, pharmaceuticals, and cosmetic products. Most of the collagen and gelatin are derived from cow (bovine) and pig (porcine) skins. Most manufacturers use collagen and gelatin produced primarily from bovine by-products. Recently, there have been concerns among consumers and regulatory bodies regarding bovine-derived products emanating from reported incidents of bovine spongiform encephalopathy (BSE). BSE (also known as Mad Cow Disease) is a chronic, degenerative neurological disorder of cattle that belongs to a family of diseases known as transmissible spongiform encephalopathies (See Mermelstein, N. H., Comprehensive BSE Risk Study Released, Food Technology, January 2002, 56 (1), 75–76, incorporated herein by reference). BSE, which is known in the art to have "specified risk materials", are transmitted from bovine tissues to humans. (See Calza L., Manfred, R., Chiodo F., Epidemics of bovine spongiform encephalopathy and new variant of Creutzfeldt-Jakob disease in humans. Most recent findings on prion disease, Recenti Prog Med. 2001 February.; 92(2): 140–9, herein incorporated by reference). Also included in that family of illnesses is vCJD, which is believed to be caused by eating neural tissue, such as brain and spinal cord from BSE-affected cattle (See Mermelstein, N. H., supra).

The public's concern and fear, especially in the European Union, about BSE is in part providing market incentives to seek alternative sources of collagen. The absence of BSE-related issues in poultry products plus the tremendous tonnage of available poultry skins make poultry skins a very desirable raw material source of collagen and gelatin.

In an embodiment of the present invention, the behavior of collagen during heating, shearing, and cooling was exploited to produce the products described herein without the use of acids and/or protease enzymes. By varying process parameters, embodiments of the present invention enables considerable flexibility in processing manipulation that can lead to the production of products of a wide range of physicochemical properties. The derived protein ingredients are highly functional providing gelling, emulsifying, firming, water-binding, and flavor-enhancing properties. There is therefore a need in the art for a process that provides an economical viable option to convert poultry skins to collagen-based functional protein ingredients of high value.

Accordingly, it is an object of the present invention to provide a process to simultaneous extract and fractionate collagen-rich proteinaceous materials and fractions thereof from poultry skins.

A further object of the invention is to provide the proteinaceous extracts as value-added protein ingredients.

A further object of the invention is to provide insoluble and soluble collagen products, collagen-based protein ingredients, water-dispersible collagen-based protein ingredients, and reduced-fat collagen-rich protein ingredients from poultry skin tissues.

Still a further object of the invention is to extract and fractionate collagen-rich proteinaceous materials and derivatives thereof from poultry skins and the development of the proteinaceous materials to collagen-based ingredients.

It is still a further object of the invention to develop the proteinaceous material to collagen-based protein ingredients that function as meat replacer, texturizer, binder/filler, stabilizer, or protective colloids in processed meat products.

It is still a further object of the invention, to produce soluble collagen (which is synonymous with commercial gelatin) by an unconventional, non-chemical technique, of recovering the liquid phase and separating it into fat and soluble collagen-rich fractions. The soluble collagen has potential utility in food (e.g., ice cream, mayonnaise dressing) and non-food applications, such as pharmaceuticals (e.g., capsules and coating for pills) and cosmetics.

Still further objects of the invention will become apparent in the following disclosure.

BRIEF SUMMARY OF THE INVENTION

The present invention is directed to a process for producing insoluble and soluble collagen products, collagen-based protein ingredients, water-dispersible collagen-based protein ingredients, and reduced-fat collagen-rich protein ingredients from poultry skin tissues. The process having features in embodiments of the present invention comprises comminuting animal skin tissue and heating the comminuted tissue to break the tissue cell membranes to release fat and protein and to form solid-phase and liquid-phase fractions. The solid-phase and liquid-phase fractions are then separated. Surprisingly, it has been found that when the solid-phase fraction is immediately cooled from above its melting temperature, a high concentration of coils are obtained which prevents refolding into native collagen, binds more water, and produces better gel strength. Additionally, it has been found that the process in accordance with the embodiments of this invention is a useful non-chemical technique to produce soluble collagen (which is synonymous with commercial gelatin) that forms a translucent soft gel at 3.5% solids at room temperature and has high water binding capacity. In the animal raw material, soluble collagen/gelatin does not exist as a native component. The conversion of insoluble collagen to soluble collagen represents the essential transformation in gelatin manufacturing. Estimated world usage of gelatin is 200,000 metric tons per year with United States usage being about 30,000 metric tons per year for food and about 10,000 metric tons per year for pharmaceutical applications (See Choi, S. S. and Regenstein, J. M., J. Food Sci. 65: 194–198, 2000, incorporated herein by reference). The solid-phase fraction is extruded, dried, and milled into powder to obtain insoluble collagen products. The liquid-phase fraction is further separated into dehydrated fat and soluble collagen. The dilute liquid soluble collagen is further concentrated and dried into powder.

These and other features, aspects and advantages of the embodiments of the invention will become better understood with reference to the following description and appended claims.

DETAILED DESCRIPTION OF THE INVENTION

According to the embodiments of the present invention poultry skin is treated to produce soluble and insoluble collagen products. As used herein, the word "poultry skin" refers to skins or skins with adhering fat and muscle flesh resulting from turkey and chicken processing. The term "poultry" refers to turkey, chicken, or any other type of fowl, with chicken being most preferred. The skin is preferably stored in a cooler (<50° Fahrenheit) prior to treatment.

In accordance with embodiments of the present invention, the skin is comminuted to increase surface area, for example by being granulated, minced, cut, chopped, or grind. The tissue should be reduced to provide a particle size diameter of between about 0.0325 inches to about 0.325 inches with about 0.125 inches to about 0.150 inches being preferred. Subsequently, the comminuted tissue enters a rendering system comprising of a melting step and a centrifugation step, both of which control fat content. The rendering of animal material especially for the recovery of fats therefrom has been practiced for centuries.

The comminuted tissue is heated by steam injection to a temperature between about 150° Fahrenheit to about 212° Fahrenheit, with the range of about 180° Fahrenheit to 195° Fahrenheit being preferred. The comminuted tissue is heated to break the tissue cell membrane to release fat and protein and to form solid-phase and liquid-phase fractions, wherein the solid-phase fractions contains insoluble collagen fiber and muscle proteins, whereas the liquid-phase fraction contains primarily a mixture of soluble collagen and fat.

Next, the solid and liquid-phase fractions are separated. This rendering step may be done in a variety of ways, all well known in the art. Preferably, the fractions are separated by centrifugation, more particularly, horizontal centrifugation. Any horizontal two-phase centrifuge such as one commercially available from Alfa Laval Separation Inc., (Greenwood, Ind.), can accomplish the separation. The use of horizontal centrifugation allows for continuous separation of a mixture under centrifugal forces. In horizontal centrifugation, solids, being of higher density, are separated out from the fluid and deposited on the bowl wall and form a sediment layer of the heavy phase containing insoluble collagen, whilst the clarified liquid layer which forms a phase inside the heavy phase, as fat and soluble collagen, is continuously discharged in the opposite direction. Due to the difference of the speed of the screw conveyer, which rotates lower than the speed of the bowl, the conveyor screw pushes the solids to the conical end of the bowl, where they are pressed through an area of the cone, where on the inside the cone narrows to a radius less than the inside radius of the liquid layer, and it ends at the solids discharge openings. The solids lift out of the liquid as they are pushed up the slanting wall of the conical section, where it is discharged.

The solid phase is stabilized against oxidation by an antioxidant as it is being discharged into the cooling chamber. Any antioxidant such as commercially available synthetic or natural antioxidant can be used. It has now been found that the solid-phase is best protected against oxidation and surprisingly exhibits longer shelf life when the antioxidant is added to a mildly hot solid-phase than to a cooled solid-phase. The solid-phase is then cooled immediately, preferably as it is removed from the centrifuge or as soon as possible for at least 30 minutes to about 2 hours from about 35° F. to about 80° F. However, from about 50° F. to about 55° F. is preferred. It should be appreciated that an important feature of this invention is the immediacy of the cooling process. Upon controlled cooling below the melting temperature, reformation of the helical form occurs, a phenomenon that accounts for collagen's ability to form cold-set thermal reversible gels. It has been found that by immediately cooling collagen to about 35° F. to about 80° F., but preferably, about 50° F. to about 55° F., a high concentration of mixtures of aggregated and three-dimensional viscoelastic fibrous network is formed that is easily extruded into noodle-like strings, capable of producing better gel strength upon drying. If cooling is not performed fast enough, a non-uniform mixtures of aggregated and viscoelastic fibrous network is formed lacking desirable noodle-like strings when extruded and ultimately lacking consistent gel strength upon drying.

The cooling process may be any method which will reduce temperature in order to induce reformation of the helical form. While the cooling process may be done indirectly using liquid nitrogen or carbon dioxide, ammonia in a stainless steel jacketed chiller is preferred.

The fat content of the solid-phase fraction is between about 0.5% to about 11%. The solid-phase fraction can then be additionally processed in a variety of ways. As related to the embodiments of the present invention, three options on how to further process the solid-phase are hereby discussed. The solid-phase fraction is extruded or conveyed onto the belt of the belt dryer, and dried to decrease the moisture content, under controlled conditions. Typically, drying the fibrous proteinaceous material at a temperature between about 200° F. to about 300° F. for a dwell time of between about 15 to about 45 minutes can control water content. Next, the collagen-rich fibrous proteinaceous material is milled into a powder (particle size=<50 mesh) to obtain an insoluble collagen product. Alternatively, the solid phase fraction is subjected to a high shear homogenization process to produce non-aggregated collagen fibrils followed by drying and milling into powder that is a water-dispersible collagen-based protein ingredient. Yet another option is where the solid-phase fraction is recycled through the heating, separation, followed by extrusion, drying and milling to produce a further reduced-fat collagen-based protein ingredient.

The liquid-phase fraction is separated by a variety of ways known to those skilled in the art, but preferably by a high-speed separator such as a vertical three-phase centrifuge such as one commercially available from Alfa Laval Separation Inc., (Greenwood, Ind.). Using a vertical three-phase centrifuge, the liquid-phase is separated into soluble collagen, fat, and sludge fractions. The dilute soluble collagen (approximately 3.5% solids or dry matter) is further concentrated, dried, and milled into powder.

Most importantly, the present invention enables considerable flexibility in process options that can lead to the production of products of a wide range of physicochemical properties. For example, the soluble collagen produced with this process, as with commercial gelatin, possesses desirable physicochemical properties to perform as a gelling agent and as a viscosity modifier in food, pharmaceuticals, and cosmetic industries. Examples of the potential applications of the soluble collagen are: (1) to bind water and fat in processed meat products; (2) to encapsulate pharmaceutical bioactives; (3) in confectionery to improve chewiness; and (4) in cosmetics as a moisturizer.

The following examples serve to better illustrate the invention described herein and are not intended to limit the invention in any way. Those skilled in the art will recognize that there are several different parameters which may be altered using routine experimentation and are intended to be within the scope of this invention.

EXAMPLE 1

Poultry skin tissues were comminuted and heated by steam injection to temperatures between from about 180° F. to about 195° F. whereupon a solid-phase and liquid-phase fraction was formed. The solid-phase fractions contained insoluble collagen fiber and muscle proteins, whereas the liquid-phase fraction contained primarily soluble collagen and trapped fat. The solid-phase fraction was then separated from the liquid-phase fraction by horizontal centrifugation. The solid-phase fraction was then immediately cooled to from about 50° F. to about 55° F. The fat content of the solid-phase is less than or equal to 11%. The solid-phase fraction was extruded, dried, and milled into powder to produce an insoluble collagen product. The liquid-phase fraction was separated by vertical centrifugation into a soluble collagen fraction, a fat fraction, and a sludge fraction. The fat was then refined to produce fat products.

EXAMPLE 2

Scale-up Plant Production of Collagen-rich Products from Poultry Skins

Fresh poultry skins resulting from the production of skinless chicken or turkey was used in a scale-up plant trial described here. Typically, the poultry skins are maintained at a temperature of less than about 38° F. and processed within 5 days after collection. Ninety thousand pounds (90,000 lbs) of fresh chicken/turkey skins were ground (comminuted) in a sanitary grinder to a particle size within the range of about 0.125 to about 0.150 inches. The comminuted chicken skin tissue was continuously conveyed into a stainless steel heating tank where it was contacted with direct steam injection at a rate of about 0.5 lb per lb of ground raw material and then heated to a temperature between about 150° F. to about 212° F. The residence time of the heated tissue in the tank ranged from about 0.5 to about 1.5 hours. Next, the solid and liquid-phase fractions were separated by a horizontal centrifuge (Model MRNX-414 Decanter Centrifuge, Alfa Laval Separation Inc., Greenwood, Ind.). The solid-phase, now reduced in fat content, was further processed to produce an insoluble collagen-rich product. At this point, the fat content of the solid-phase ranged between about 0.5% to about 11% depending upon the desired finished product characteristics. The following must occur to assure a functional and stable finished product. First, a rosemary extract antioxidant (approximately 0.0625%) was added to the hot solid-phase fraction as it exited into the cooling chamber. Next, the solid-phase fraction was cooled immediately in a paddle cooler (Chiller Komline Sander) at a rate of about 600 pounds per hour. The cooled poultry skin tissue was then extruded or conveyed onto the belt of the belt dryer, and dried to decrease the moisture content, under controlled conditions. Typically, drying the fibrous proteinaceous material at a temperature between about 200° F. to about 300° F. for a dwell time of between about 15 to about 45 minutes can control water content. The collagen-rich proteinaceous material was milled (Fitz Mill) at a rate of 1500 pounds per hour into a powder (particle size=<50 mesh) to obtain an insoluble collagen product. The product is a light tan powdered product with a mild chicken or turkey flavor. The composition and/or characteristics of the raw material and finished product are given in Tables 1 and 2.

TABLE 1

Composition* of raw material and turkey skins

| Composition (%) | Chicken skins | Turkey skins |
| --- | --- | --- |
| Protein | 7.2 | 12.3 |
| Fat | 41.7 | 31.4 |
| Moisture | 52.1 | 55.9 |
| Ash | 0.3 | 0.3 |
| Total Solids | 49.2 | 44.0 |

*Average values of 3 plant trials

TABLE 2

Characteristics* of insoluble collagen Product

| Parameters | Chicken skin product | Turkey skin product |
|---|---|---|
| Composition (%) | | |
| Protein | 69.4 | 78.0 |
| Fat | 28.5 | 21.5 |
| Moisture | 1.3 | 1.0 |
| Ash | 2.3 | 1.6 |
| Collagen (%)** | | |
| Gel Strength (g) | 292 | 275 |
| Microbiological: | | |
| Standard Plate Count (SPC) | 15,000 CFU/gram | 15,000 CFU/gram |
| Salmonella | Negatives/25 grams | Negative/25 grams |

*Average value of 3 plant trials; **Hydroxyproline content times a factor of 8.

The collagen content was derived from the amino acid composition presented in Table 3. The product "as is" contained hydroxyproline contents of 3.19 and 2.94% for chicken- and turkey-based collagen, respectively, which translated to a collagen content of 25.5% and 23.5%, respectively. Note, if based on 100% protein, as presented in Table 3, the hydroxyproline contents are higher (4.62% and 4.67%, respectively) as would be expected. The gel strength is an index of water binding capability and application performance when used as meat replacer, texturizer, binder or filler in processed meats.

The performance of the collagen-rich products described in Example 2 have been tested in various processed meat products such as breakfast sausages, nuggets, breaded patties, and burgers. Some performance tests are described in Example 3 below.

TABLE 3

Amino acid composition (g/100 g protein) of insoluble collagen products from poultry skins

| Amino acid | Chicken skin product | Turkey skin product |
|---|---|---|
| Alanine | 7.14 | 6.75 |
| Arginine | 7.23 | 7.17 |
| Aspartic acid | 7.85 | 8.18 |
| Cysteine | 0.58 | 0.58 |
| Glutamic acid | 12.24 | 12.59 |
| Glycine | 12.82 | 11.57 |
| Histidine | 2.17 | 2.46 |
| Hydroxyproline | 4.62 | 4.67 |
| Isoleucine | 3.51 | 3.45 |
| Leucine | 6.30 | 6.26 |
| Lysine | 7.10 | 8.52 |
| Methionine | 2.09 | 2.13 |
| Phenylalanine | 3.42 | 3.26 |
| Proline | 7.55 | 7.33 |
| Serine | 3.95 | 4.10 |
| Threonine | 4.20 | 3.93 |
| Tryptophan | 0.00 | 0.00 |
| Tryosine | 2.54 | 2.59 |
| Valine | 4.69 | 4.46 |
| Total | 100 | 100 |

EXAMPLE 3

Application of the Collagen-rich Product (as Described in Example 2) in Processed Meats The following exemplifies the utility of the chicken skin collagen-rich product in fully cooked chopped and formed chicken patty to provide cost savings by replacing a portion of the chicken breast meat with the chicken skin collagen-rich product.

The formulation shown in Table 4 was processed according to the procedure recommended for this type of meat product. The test showed that the use of the collagen skin product in a fully cooked, chopped, and formed chicken patty resulted in a moisture meat product with a more natural chicken flavor than the control. Furthermore, a cost in savings was obtained when a portion of the meat block was replaced with chicken skin collagen-rich product, based on treatment cost per pound of product produced.

TABLE 4

Formulation for fully cooked chopped and formed chicken patty

| Ingredient | Control (%) | Test (%) |
|---|---|---|
| Chicken breast pieces | 44.32 | 41.82 |
| Chicken breast chunks | 44.32 | 41.82 |
| Seasoning | 2.00 | 2.00 |
| Water | 8.40 | 12.40 |
| Chick skin product | 0.00 | 1.00 |
| Salt | 0.48 | 0.48 |
| Phosphate | 0.48 | 0.48 |
| Total | 100.00 | 100.00 |

The following exemplifies the utility of the chicken skin collagen-rich product in fully cooked chopped buffalo wings to increase cooked yields while providing a cost in savings by replacing a portion of the meat block.

The formulation shown in Table 5 was processed according to the procedure recommended for this type of meat product. The test showed that when a portion of the meat block was replaced with collagen skin collagen-rich product and water in fully cooked buffalo wings, cooked yields were increased (approximately 5.2%) and cost savings achieved. Furthermore, the use of the test product resulted in a 40% reduction in tumbling time.

TABLE 5

Formulation for fully cooked buffalo wings

| Ingredient | Control (%) | Test (%) |
|---|---|---|
| Chicken wings | 77.76 | 72.76 |
| Water | 11.12 | 15.12 |
| Buffalo seasoning | 11.12 | 11.12 |
| Chicken skin product | 0.00 | 1.00 |
| Total | 100.00 | 100.00 |

The following formulation exemplifies the utility of the chicken skin collagen-rich product in fully cooked chicken breast fillet to increase cooked yield while providing cost savings by replacing a portion of the breast meat.

The formulation shown in Table 6 was processed according to the procedure recommended for this type of meat product. The use of collagen skin collagen-rich product in fully cooked chicken breast fillet resulted in increased cooked yield (approximately 3.8%) and a cost in savings. Furthermore, the use of the test product resulted in a 40% reduction in tumbling time.

TABLE 6

Formulation for fully cooked chicken breast fillet

| Ingredient | Control (%) | Test (%) |
|---|---|---|
| Tom breast fillets | 89.29 | 84.29 |
| Water | 9.78 | 13.78 |
| Chicken skin product | 0.00 | 1.00 |
| Salt | 0.50 | 0.50 |
| Phosphate | 0.43 | 0.43 |
| Total | 100.00 | 100.00 |

EXAMPLE 4

The process of Example 2 was followed except that the solid-phase fraction was further subjected to a high shear homogenization process to produce non-aggregated collagen fibrils followed by drying and milling into powder that is a water-dispersible collagen-based protein ingredient.

EXAMPLE 5

The process of Example 2 was followed except that the solid-phase fraction was recycled through the steps of heating, separation, and cooling, under controlled conditions, then extruded, dried, and milled to produce a further reduced-fat collagen-based protein ingredient.

EXAMPLE 6

The process of Example 1 was followed except that the liquid-phase fraction was separated by a variety of ways known to those skilled in the art. Separation preferably could be achieved by a high-speed separator such as a three-phase vertical disk stack separator for separating animal fat and water such as Model AFPX-513XGD-74CG, commercially available from Alfa Laval Separation Inc., (Greenwood, Ind.). Using such a centrifuge, the liquid-phase is separated into soluble collagen, fat, and sludge fractions. In this test, Westfalia is typically low in moisture (<0.5%) and composed of 29% saturated fatty acid, 39% oleic acid, and 17% linoleic acid.

The dilute soluble collagen (approximately 3.5% solids or dry matter) was further concentrated, dried, and milled into powder. The soluble collagen powder product is white to off-white in color. The chemical composition is given in Table 8.

TABLE 8

Composition of soluble collagen from chicken skins

| Protein | 94.0 |
|---|---|
| Fat | 1.5 |
| Moisture | 2.5 |
| Ash | 2.0 |

EXAMPLE 7

Use of Recovered Soluble Collagen to Improve Yield of Insoluble Collagen Product The process of Example 2 and 5 were followed except that the soluble collagen fraction (approximately 3.5% solids) was recovered and allowed first to form a gel upon standing and then added back to the solid-phase fraction, then extruded, dried, and milled into powder.

As can be seen from the foregoing, the invention accomplishes at least all of its objectives.

What is claimed is:

1. A process for treating animal skin tissues to extract and fractionate collagen-rich proteinaceous materials comprising:
    comminuting animal skin tissues;
    heating the comminuted skin tissues without acids or a proteolytic enzyme to form a solid-phase fraction comprising insoluble collagen fiber and muscle and a liquid-phase fraction comprising soluble collagen and trapped fat;
    separating the solid phase fraction and the liquid-phase fraction;
    cooling the solid-phase fraction immediately to produce a high concentration of coils;
    extruding, drying, and milling the solid-phase into a powder;
    refining the liquid-phase fraction;
    precipitating collagen fibers from the liquid-phase; and
    drying the collagen fibers.

2. A process as claimed in claim 1 in which the skin tissues are comminuted by granulating, chopping, mincing, cutting, or grinding.

3. A process as claimed in claim 1 in which the skin tissues comprise tissue from poultry.

4. A process as claimed in claim 1, further comprising adding an antioxidant to the solid-phase fraction.

5. A process as claimed in claim 4, wherein the antioxidant is a rosemary extract antioxidant.

6. A process as claimed in claim 4, wherein the antioxidant is added to the solid phase fraction prior to cooling the solid phase fraction.

7. A process as claimed in claim 1 in which the comminuted skin tissues are treated with heat at a temperature between about 150° F. to about 212° F.

8. A process as claimed in claim 7 in which the heat is by steam injection.

9. A process as claimed in claim 8 in which the temperature is preferably between about 180° F. to about 195° F.

10. A process as claimed in claim 7 in which the heated comminuted skin tissues are separated to form a solid-phase fraction and a liquid-phase fraction.

11. A process as claimed in claim 10 in which separation is by centrifugation.

12. A process as claimed in claim 11 wherein centrifugation is horizontal centrifugation.

13. A process as claimed in claim 10 in which the liquid-phase fraction is separated by centrifugation into a soluble collagen fraction, a fat fraction, and a sludge fraction.

14. A process as claimed in claim 13 in which the centrifugation is vertical centrifugation.

15. A process as claimed in claim 13 in which the fat fraction has water removed.

16. A process as claimed in claim 13 in which the soluble collagen is precipitated to form a collagen fiber.

17. A process as claimed in claim 16 in which the collagen fibers are dried and milled into powder.

18. A process as claimed in claim 1 in which the solid-phase is immediately cooled for at least 30 minutes to about 2 hours to a temperature from about 35° F. to about 80° F.

19. A process as claimed in claim 18 in which the cooling temperature is about 50° F. to about 55° F.

20. A process as claimed in claim 18 in which the solid-phase has a fat content of less than or equal to about 11%.

21. A process as claimed in claim 18 in which the solid-phase is extruded, dried, and milled into powder.

22. A process as claimed in claim 18 in which the solid-phase is alternatively subjected to a high shear homogenization process, dried, and milled into powder.

23. A process as claimed in claim 18 in which the solid-phase is cooled using at least one of the materials selected from the group consisting of liquid nitrogen, carbon dioxide, and ammonia.

24. A process as claimed in claim 23 in which cooling is by ammonia.

25. A process as claimed in claim 18 in which the solid-phase is recycled through the heating and separation steps, and immediately cooled.

26. A process as claimed in claim 25 further comprising extruding, drying, and milling the solid-phase.

* * * * *